(12) United States Patent
Peters et al.

(10) Patent No.: US 9,506,843 B2
(45) Date of Patent: Nov. 29, 2016

(54) PERSONAL NANOPARTICLE RESPIRATORY DEPOSITIONS SAMPLER AND METHODS OF USING THE SAME

(71) Applicant: UNIVERSITY OF IOWA RESEARCH FOUNDATION, Iowa City, IA (US)

(72) Inventors: Thomas Peters, Iowa City, IA (US); Lorenzo Cena, North Liberty, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 509 days.

(21) Appl. No.: 13/769,565

(22) Filed: Feb. 18, 2013

(65) Prior Publication Data

US 2013/0220034 A1 Aug. 29, 2013

Related U.S. Application Data

(60) Provisional application No. 61/599,683, filed on Feb. 16, 2012.

(51) Int. Cl.
*G01N 1/22* (2006.01)
(52) U.S. Cl.
CPC .......... *G01N 1/2208* (2013.01); *G01N 1/2273* (2013.01); *G01N 2001/2276* (2013.01)
(58) Field of Classification Search
CPC ............. G01N 1/2208; G01N 1/2273; G01N 2001/2276
USPC .......... 73/28.01, 28.04, 28.05, 28.06, 863.22
See application file for complete search history.

(56) References Cited

U.S. PATENT DOCUMENTS

| | | | | |
|---|---|---|---|---|
| 3,693,410 A | * | 9/1972 | Robrecht et al. | 73/28.01 |
| 3,922,905 A | * | 12/1975 | Roth | 73/28.04 |
| 3,949,594 A | * | 4/1976 | Treaftis et al. | 73/28.04 |
| 3,966,439 A | * | 6/1976 | Vennos | 73/863.22 |
| 4,080,832 A | * | 3/1978 | Moody et al. | 73/863.23 |
| 4,178,794 A | * | 12/1979 | Jugle et al. | 73/863.25 |
| 4,249,655 A | * | 2/1981 | Patureau et al. | 209/31 |
| 4,350,507 A | * | 9/1982 | Greenough et al. | 73/863.23 |
| 4,640,140 A | * | 2/1987 | Burghoffer et al. | 73/863.22 |
| 4,796,475 A | * | 1/1989 | Marple | 73/863.22 |
| 5,370,004 A | * | 12/1994 | Bossart et al. | 73/863.23 |
| 6,401,520 B1 | * | 6/2002 | Volkwein et al. | 73/28.03 |
| 6,685,759 B2 | * | 2/2004 | Dahlin et al. | 55/465 |
| 6,692,553 B2 | * | 2/2004 | Jordan et al. | 95/285 |
| 6,786,105 B1 | * | 9/2004 | Sioutas | 73/863.22 |

(Continued)

FOREIGN PATENT DOCUMENTS

JP 46-6037 * 7/1967

OTHER PUBLICATIONS

Furuuchi, M. et al.,"Development and Performance Evaluation of Air Sample with Inertial Filter for Nanoparticle Sampling", Aerosol and Air Quality Research, vol. 10, (2010), pp. 185-192.*

(Continued)

*Primary Examiner* — Daniel S Larkin
(74) *Attorney, Agent, or Firm* — Smith, Gambrell & Russell

(57) ABSTRACT

A personally portable nanoparticle respiratory deposition (NRD) sampler configured to collect nanoparticles based upon a sampling criterion. In an aspect, the NRD sampler has an impactor stage, and a diffusion stage. In another aspect, the NRD sampler includes a particle size separator in addition to an impactor stage and a diffusion stage.

20 Claims, 15 Drawing Sheets

(56) References Cited

U.S. PATENT DOCUMENTS

| | | | |
|---|---|---|---|
| 7,334,453 B2* | 2/2008 | Trakumas et al. | 73/28.05 |
| 7,597,015 B2* | 10/2009 | Harley | 73/865.5 |
| 8,459,098 B2* | 6/2013 | Lee et al. | 73/31.07 |
| 8,689,648 B1* | 4/2014 | Heff | 73/863.22 |
| 2008/0196484 A1 | 8/2008 | Gorbunov | |
| 2012/0160010 A1* | 6/2012 | Chen et al. | 73/28.04 |

OTHER PUBLICATIONS

Gorbunov, B. et al.,"A Novel Size-Selective Airborne Particle Size Fractionating Instrument for Health Risk Evaluation", Ann. Occup. Hyg., vol. 53, No. 3, (2009), pp. 225-237.*

Hering, S.V. et al., "Design and Evaluation of New Low-Pressure Impactor. I.", Environmental Science & Technology Research, vol. 12, No. 6, (Jun. 1978), pp. 667-673.*

Gorner, P. et al., "Study of Fifteen Respirable Aerosol Samplers Used in Occupational Hygiene", Ann. Occup. Hyg., vol. 45, No. 1, (2001), pp. 43-54.*

Demokritou, P. et al., "A Compact Multistage (Cascade) Impactor for the Characterization of Atmospheric Aerosols", Journal of Aerosol Science, vol. 35, (2004), pp. 281-299.*

Misra, C. et al., "A High Flow Rate, Very Low Pressure Drop Impactor for Inertial Separation of Ultrafine from Accumulation Mode Particles", Journal of Aerosol Science, vol. 33, (2002), pp. 735-752.*

"Personal Cyclone Sampler", Sensidyne, Gil 2320 Rev B 9901, (1999) pp. 1-2.*

Cena, L.G. et al., "A Personal Nanoparticle Respiratory Deposition (NRD) Sampler", Environmental Science and Technology, vol. 45, (2011), pp. 6483-6490.*

* cited by examiner

KEY
□ is Vt=500 ml, Q=250 ml/s; Δ is Vt=1000 ml, Q=250 ml/s; O is Vt=1000 ml, Q=500 ml/s. Closed symbols are data of Kim and Hu (1998) and Kim and Jaques (2000): ■ is Vt=500 ml, Q=250 ml/s; ▲ is Vt=1000 ml, Q=250 ml/s; ● is Vt=1000 ml, Q=500 ml/s. Vt = tidal breathing volume and Q = air flow rate.

Experimental setup for the diffusion stage deposition tests

Collection efficiency by size of the impaction stage

NPM Sampling Criterion, ICRP total respiratory deposition, and effective deposition on the diffusion stage of the NRD sampler.

PERSONAL NANOPARTICLE RESPIRATORY DEPOSITIONS SAMPLER AND METHODS OF USING THE SAME

CLAIM OF PRIORITY

This application claims priority from U.S. Provisional Patent Application No. 61/599,683 filed on Feb. 16, 2012, which is relied upon and incorporated herein in its entirety by reference.

STATEMENT OF GOVERNMENT SUPPORT

This invention was made with United States government support under Grant No. 1R21OH008757-01 awarded by the Centers for Disease Control. The government has certain rights in this invention.

BACKGROUND

Field of Invention

This invention relates to devices and methods for selectively collecting nanoparticles. More particularly, this invention relates to devices and methods for selectively collecting nanoparticles in a manner that relates physiologically to the human respiratory system.

Workers produce and handle engineered nanomaterials in substantial quantities in the manufacture of hundreds of commercial products. Exposure through inhalation of these materials is a primary concern for worker health and safety because of the sensitivity of the respiratory system. The airborne nanoparticle component ($\leq 100$ nm) is of particular concern because nanoparticles can elicit substantially greater toxic effects than larger particles of the same composition. Moreover, nanoparticles may translocate from the respiratory tract to other organs and the blood stream. The National Institute for Occupational Safety and Health (NIOSH) has proposed draft guidelines for ultrafine titanium dioxide, which includes recommended exposure limits and exposure assessment method. The proposed exposure assessment method relies on traditional 8-hr, filter-based, personal respirable sampling.

Size-selective samplers are used to collect particles with efficiencies that represent how particles enter into or deposit within the respirator system. Respirable samplers are used to collect particles with efficiencies that approximate the fraction of aerosol that, once inhaled, can penetrate into the gas-exchange region of the respiratory tract. They are designed to match a specific sampling criterion, which defines collection efficiency of particles to the filter as 50% for 4 µm particles and 100% for particles smaller than 1 µm. By this definition, respirable samplers must prevent the collection of larger particles (>10 µm) that may exist in the environment while selectively sampling only these smaller particles at the specified collection efficiencies. However, when aerosols include both nanoparticles and respirable particles, the mass measured from a sample collected using a respirable sampler will be dominated by the larger, non-nano-sized particles. Hence, in many occupational environments where both nanoparticles and respirable particles coexist, the respirable sampler has limited usefulness in quantifying nanoparticle exposures.

To overcome this problem for assessing titanium dioxide nanoparticle exposures, NIOSH recommends both mass-based respirable sampling coupled with sizing and compositional analysis performed by electron microscopy with energy dispersive x-ray spectroscopy to determine the fraction of titanium dioxide that is associated with nanoparticles. However, there are no standard methods for this analysis, and electron microscopy is particularly expensive (>$300 per sample) compared to bulk analysis methods (~$30 per sample). A personal sampling method that removes larger particles and only collects nanoparticles would streamline exposure assessment.

Wire mesh screens have been used successfully to preferentially collect nanoparticles. The Brownian motion of particles smaller than 300 nm enhances their deposition onto the surface of the wires by diffusion. Stainless steel screens have typically been used, although they are incompatible with bulk analysis techniques that require dissolution of the collection media. Previous work has been devoted to developing a size-selective sampler that uses an impactor to remove large particles and nylon mesh screens to collect nanoparticles. This work analyzed nanoparticles by treating the nylon mesh screens in aqua regia and subjecting them to microwave digestion. While this technique provides a method for separating and analyzing nanoparticles from other aerosol components, its large size limits this sampler to area sampling and does not collect particles with physiological relevance.

Because exposure assessors have a need to characterize exposures to nanoparticles in environments where other size-fractions may exist, a need exists to develop a sampler that can preferentially eliminate large particles and allow quantification of small, nanoparticle aerosols. An ideal sampler would be portable, allow placement within the breathing zone of a worker and collect nanoparticles in a way that mimics their respiratory deposition. By capturing only nanoparticles on the sampling media, cost-efficient bulk analysis techniques could then be used to estimate the amount of deposited nanomaterials.

Known low pressure impactors operate at pressures substantially lower than atmospheric to reduce drag forces and allow collection of particles as small as 50 nm. Micro orifice impactors employ up to a few thousand small (40-200 µm) round nozzles to achieve smaller cutoff diameters. These impactors achieve sharp collection efficiency curves ($\sigma=1.2$); however, they require rather large pumps to achieve high flow rates and low pressures, making them less portable.

Accordingly, there is a need in the pertinent art for a personal nanoparticle respiratory deposition (NRD) sampler capable for deployment as a full-shift, personal sampler that selectively collects nanoparticles apart from larger particles in a workplace atmosphere. There is a further need for NRD samplers that are designed to collect nanoparticles as they deposit in the respiratory tract, thereby providing a physiologic relevance to the NRD sampler's performance. There is still a further need for portable NRD samplers that are capable of achieving sharp collection efficiency curves.

SUMMARY

Described herein is a personal nanoparticle respiratory deposition (NRD) sampler that selectively collects nanoparticles in the manner in which they are deposited in the respiratory system of a subject. The NRD sampler has a respirable cyclone fitted with an impactor and a diffusion stage containing a plurality of nylon-mesh screens, such as, for example, eight nylon-mesh screens. The NRD sampler operates at a specific air flow rate and is configured for positioning on clothing worn by the subject, such as, for example, a lapel. In operation, the effective deposition of nanoparticles on the mesh screens of the diffusion stage (with the respirable cyclone and the impactor present) match the deposition in all regions of the respiratory system, as defined by the International Commission on Radiological Protection for particles smaller than 300 nm.

The NRD sampler is configured for a variety of applications, including assessment of personal exposure to nanoparticles in the workplace and environment for medical surveillance, as well as epidemiological studies. The NRD sampler collects nanoparticles separately from other particles that are in the air, thereby permitting more accurate nanoparticle mass measurements than those permitted by conventional respirable samplers, which provide samples including both nanoparticles and larger particles that obscure the mass of the nanoparticles in the sample.

BRIEF DESCRIPTION OF THE FIGURES

These and other features of the preferred embodiments of the invention will become more apparent in the detailed description in which reference is made to the appended drawings wherein.

DETAILED DESCRIPTION

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, and, as such, can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms “a,” “an” and “the” include plural referents unless the context clearly dictates otherwise. Thus, for example, reference to “a delivery conduit” can include two or more such delivery conduits unless the context indicates otherwise.

Figure 13:
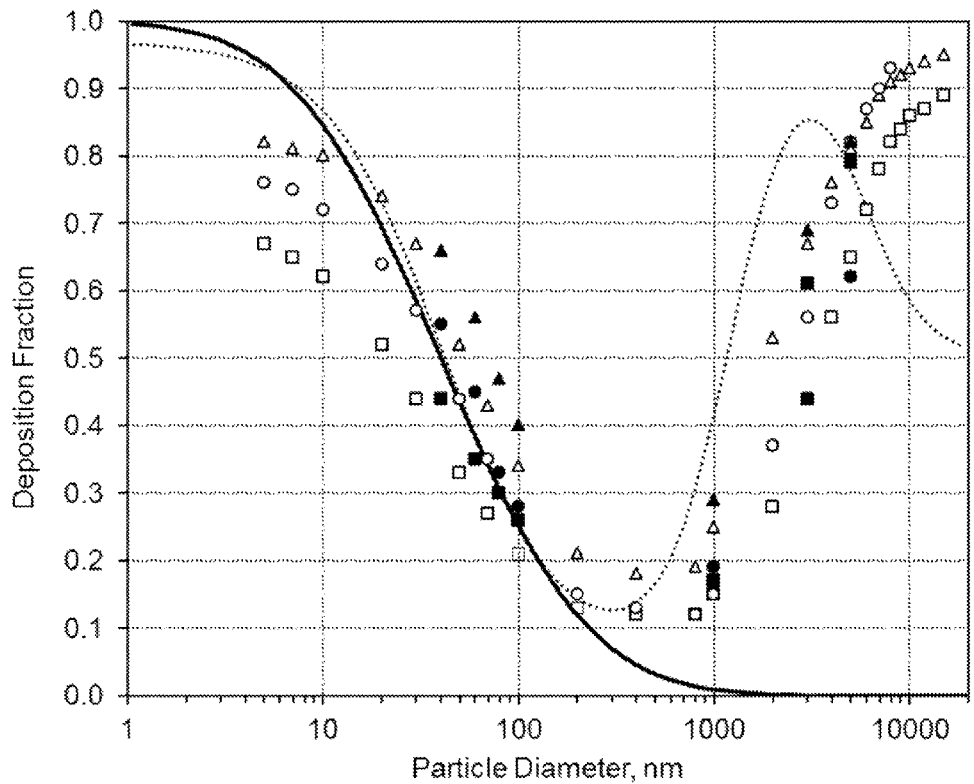
FIG. 13 illustrates a graphical representation of NPM criterion using the International Commission on Radiological Protection according to an aspect of the invention.

As used herein, the terms “optional” or “optionally” mean that the subsequently described event or circumstance may or may not occur, and that the description includes instances where said event or circumstance occurs and instances where it does not.

It is contemplated that the disclosed devices and systems can comprise elements of the devices and systems described in U.S. Patent Publication No. 2008/0196484, the disclosure of which is incorporated herein in its entirety.

In one embodiment, and with reference to FIGS. 1-3, the invention relates to a nanoparticle respiratory deposition sampler 10. As shown in FIGS. 1-3, in various aspects, the nanoparticle respiratory deposition (NRD) sampler 10 can comprise three primary components assembled in series: a particle size separator 100; an impactor stage 200; and a diffusion stage 300.

In an aspect, the NRD sampler 10 and its components can be configured to operate at a selected sampling criterion. The sampling criterion can be selectively varied depending upon the particular application in which the NRD sampler 10 is used. In exemplary aspects, it is contemplated that the selected sampling criterion can serve as a target curve for the NRD sampler 10. In an exemplary aspect, the selected sampling criterion can be a nanoparticulate matter (NPM) sampling criterion. In one aspect, the mathematical form of the NPM sampling criterion can be generally analogous to size-selective occupational sampling criteria (e.g., respirable). However, unlike other known criteria that are based on penetration of particles into specific respiratory regions (e.g., alveolar and thoracic) within a subject, it is contemplated that the NPM sampling criterion of the disclosed NRD sampler 10 can specify that the sampler performance (i.e., collection efficiency of the diffusion stage) should match the deposition of particles throughout the respiratory tract of a subject thereby providing a rational target for the development of samplers specific for assessing particular nanoparticle exposures. Discussed in more detail below, the NPM criterion can be designed to match the deposition of particulates in the respiratory system as observed in past research, as illustrated in FIG. 13. Such criteria can include, but are not limited to, criteria specified by the American Conference of Governmental Industrial Hygienists (ACGIH), and similar organizations.

It is contemplated that the particle size separator 100 can be configured to reduce the loading on the impaction stage of the NRD sampler 10. In one exemplary aspect, the particle size separator 100 can be a respirable cyclone 100, such as, for example and without limitation, a respirable aluminum cyclone 100. In another exemplary aspect, the particle size separator 100 can be a 25-mm respirable cyclone 100, such as, for example and without limitation, SKC Inc. (Eighty Four, Pa.) Model No. 225-01-01 respirable cyclone 100. In a further exemplary aspect, the particle size separator 100 can be a 37-mm nylon respirable cyclone 100. In other embodiments of the present invention, the particle size separator 100 can include, but are not limited to, GS-1 and GS-3 respirable cyclones from SKC Inc., and the 10-mn Nylon Don-Oliver Cyclone from Zefon. However, it is contemplated that the particle size separator 100 can be any conventional respirable cyclone 100. It is further contemplated that the particle size separator 100 can comprise other suitable materials and other suitable dimensions depending on the particular application for which the NRD sampler 10 is to be used.

The particle size separator 100, shown as a respirable cyclone 100 in FIGS. 1-4, includes a hollow tubular body 110 having an air inlet 120, the air inlet 120 providing access into the interior of the tubular body 110. The tubular body 110 includes a grit pot 130 at one end, where the grit pot 130 can be configured to be removable. A cyclone 140 can be found at an end of the tubular body 110 of the particle size separator 100 opposite the grit pot 130. The cyclone 140 includes an opening 142 to the interior of the tubular body 110. Air is drawn into the particle size separator 100 through the air inlet 120, traveling through the tubular body 110 and exiting out of the opening 142 of the cyclone 140 towards the impactor stage 200, discussed below.

In addition, the exterior of the cyclone 140 can include a combination groove/O-ring 144 to secure the impactor stage 200 securely to the particle size separator 100 at the cyclone 140. The combination groove/O-ring 144 creates an air-tight seal between the impactor stage 200 and the particle size separator 100. Other various fastening means can be included on the body of the cyclone 140 in order to facilitate coupling with the impactor stage 200. Such fastening means can include matching threading surfaces, a slot/tab combination, and the like. Adjacent the cyclone 140 and between the tubular body 110 is a flange 146 to provide a surface on which the impactor stage 200 can rest when secured.

In one aspect, it is contemplated that, after air is drawn through the particle size separator 100 through the air inlet 120, the particle size separator 100 can be configured to remove particles larger than a selected respirable sampler criterion and transport a respirable fraction of the particles to the impaction stage 200. As air enters into the tubular body 110, the air is spun within the interior of the tubular body, causing the larger particles to contact the interior walls of the tubular body 110 and begin to migrate towards the grit pot 130. The grit pot 130 is configured to be removable in order to dispose of the collected particles after use of the NRD sampler 10.

The speed at which the air flows through the particle size separator 100, as well as the dimensions of the particle size separator 100, controls the size of the particles being removed from the air within the particle size separator 100. In an exemplary aspect, utilizing a 25 mm respirable cyclone 100 with an airflow rate (Q) of 2.5 Liters per minute (Lpm) (controlled by a pump 400, as shown in FIG. 12 and discussed below) results in particles having an aerodynamic diameter of 2 μm passing through the particle size separator 100 at a rate of 91%, whereas particles having an aerodynamic diameter of 8 μm passing through at a rate of 5%. In other aspects, by utilizing particle size separators 100 with different dimensions and varying the air flow rate, different particle sizes, and percentages, can be removed from the air flowing through the NRD sampler 10 at the particle size separator 100.

Alternatively, in other aspects, it is contemplated that the particle size separator 100 can comprise any conventional means for removing particles larger than a particular size, such as, for example and without limitation, a cyclone other than a respirable cyclone (e.g., a cyclone with a 50% cutoff diameter smaller than 4 μm), an impactor, a virtual impactor, and the like. In other aspects, it is contemplated that the NRD sampler 10 may not utilize a particle size separator 100. In an aspect, the NRD sampler 10 may be used in a setting that does not have particulates of a large size, and therefore does not require the use of a particle size separator 100. However, in dusty environments, it is contemplated that a particle size separator 100 is utilized by the NRD sampler 10 to reduce the load on the impactor stage 200.

In another aspect, the NRD sampler 10 can utilize the particle size separator 100 in order to operate as a respirable sampler in addition to a nanoparticle sampler. In such an aspect, the particle size separator 100 removes a portion of larger particles that would not ordinarily make it into a respiratory system, leaving the combination of the remaining particles collected in the impactor stage 200 and diffusion stage 300 as the respirable mass, and the amount collected in the diffusion stage 300 as the nanoparticle mass.

Referring to FIGS. 1-3, the impactor stage 200 is coupled to the particle size separator 100. The impactor stage 200 can include an impactor 210, an impactor substrate 240 and a spacer 280. As illustrated in FIGS. 1-3 and 5, the impactor 210 includes an outer housing 212 having a bottom end 214 and a top end 216. As shown in FIGS. 1-2, the housing 212 has a cylindrical shape. While the preferred shape of the housing 212 is cylindrical, the shape of the housing 212 can vary dependent upon the environment in which the NRD sampler 10 is used. The bottom end 214 of the housing 212 is configured to be coupled to the particle size separator 100. As shown in FIGS. 1-3, the bottom end 214 of the housing 212 is configured to connect to the cyclone 140 of the particle size separator 100. In some embodiments, the combination groove/O-ring 144 can be used to secure the cyclone 140 to the bottom end 214 of the cylindrical housing 212. Further, in some embodiments, additional fastening means (e.g., matching threaded surfaces and/or matching slot/gap configurations) may be used.

Opposite the bottom end 214 is the top end 216 of the housing 212, as shown in FIGS. 1-3 and 5. Similar to the cyclone 140 of the particle size separator 100, the top end 216 can include fastening means 218 to secure to other components, including the spacer 280. The fastening means 218 can include, but are not limited to, a groove/O-ring combination 218 (as shown in FIG. 2), threaded surfaces, and/or a gap/slot combination, or a combination of various fastening means and methods known in the art. However, it is preferable that any fastening means employed is removable and recoupable, allowing for the reuse of the components. The top end 216 of the housing 212 of the impactor 210 includes a surface 220 on which the impaction substrate 240 can rest when the impactor stage 200 is fully assembled. The housing 212 of the impactor 210 can include a ledge 222 that provides a surface for which the bottom of the spacer 280 to rest when attached to the impactor 210.

Figure 2:
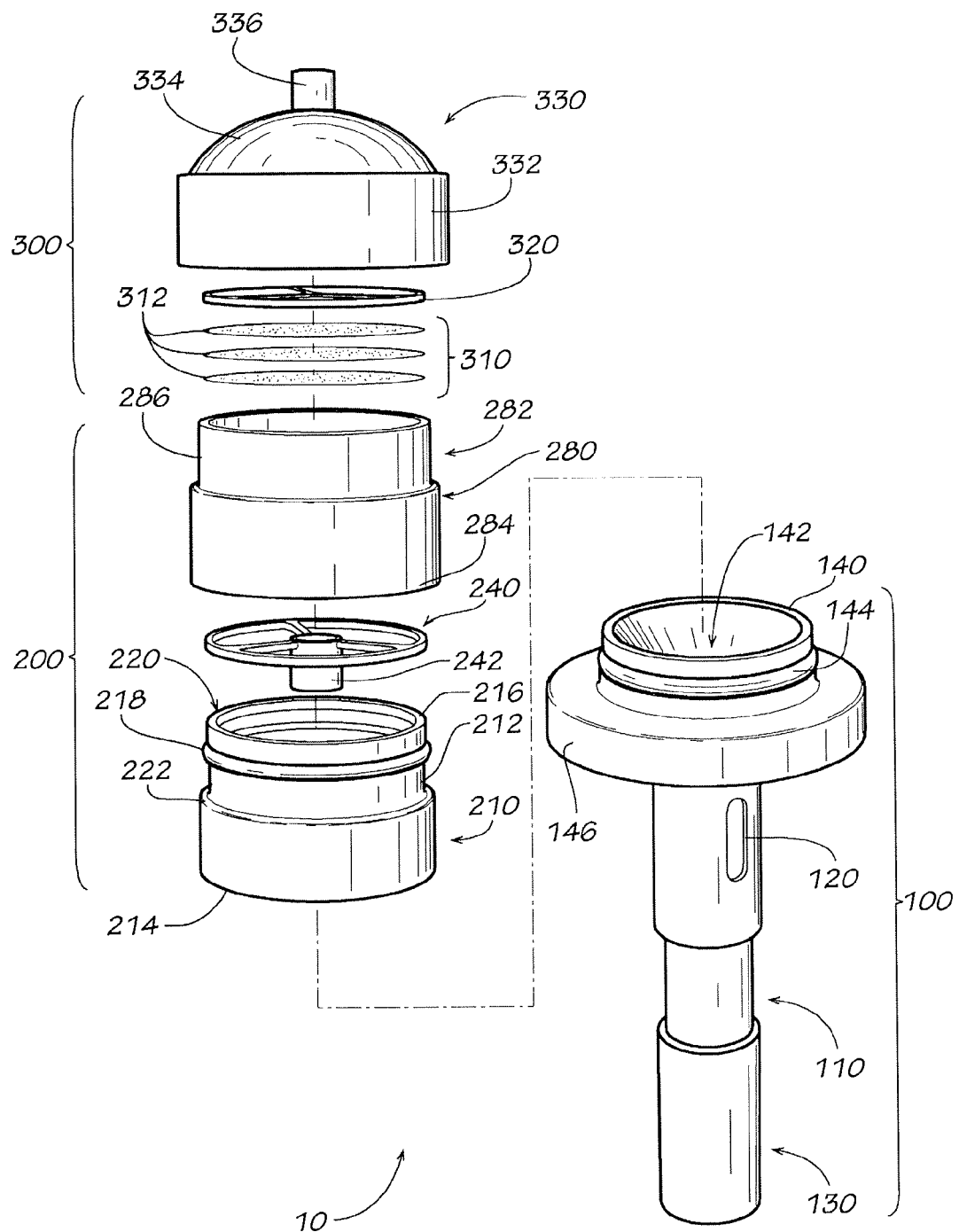
FIG. 2 illustrates a perspective exploded view of the nanoparticle respiratory deposition sampler of FIG. 1.
Figure 3:
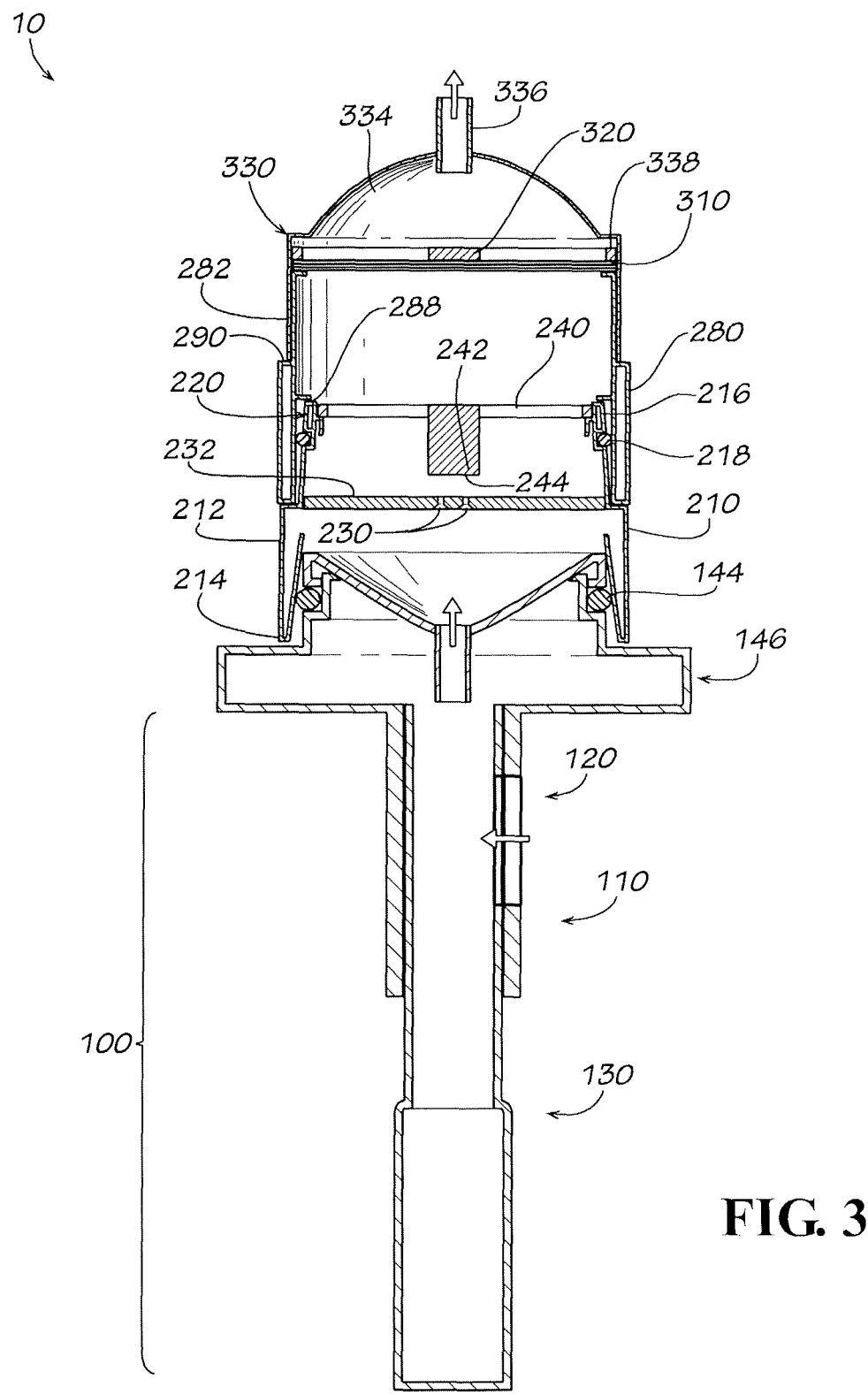
FIG. 3 illustrates a cross sectional view of the nanoparticle respiratory deposition sampler of FIG. 1 along line 3-3.
Figure 4:
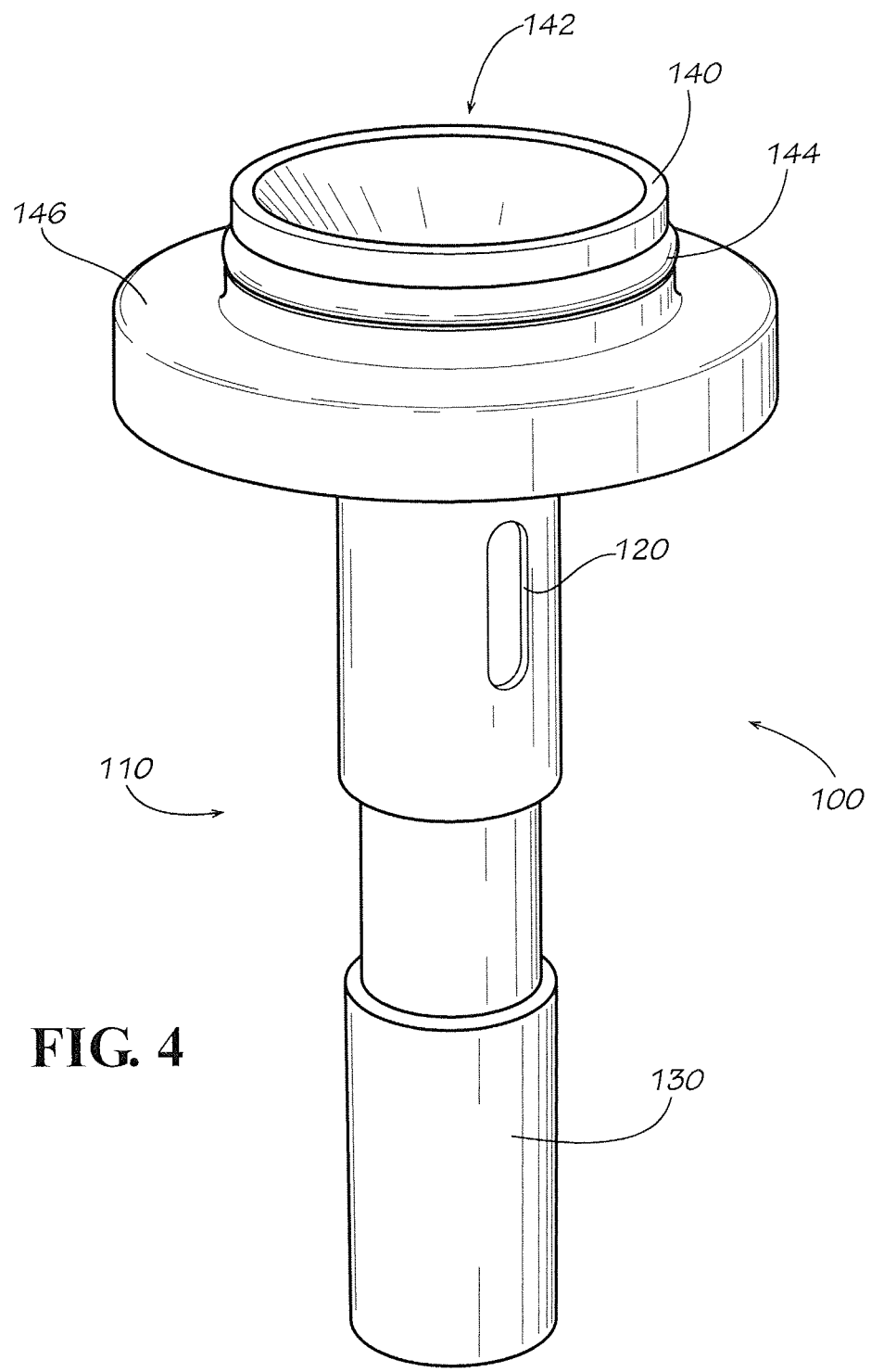
FIG. 4 illustrates a front perspective view of the particle size separator of FIG. 1.
Figure 5:
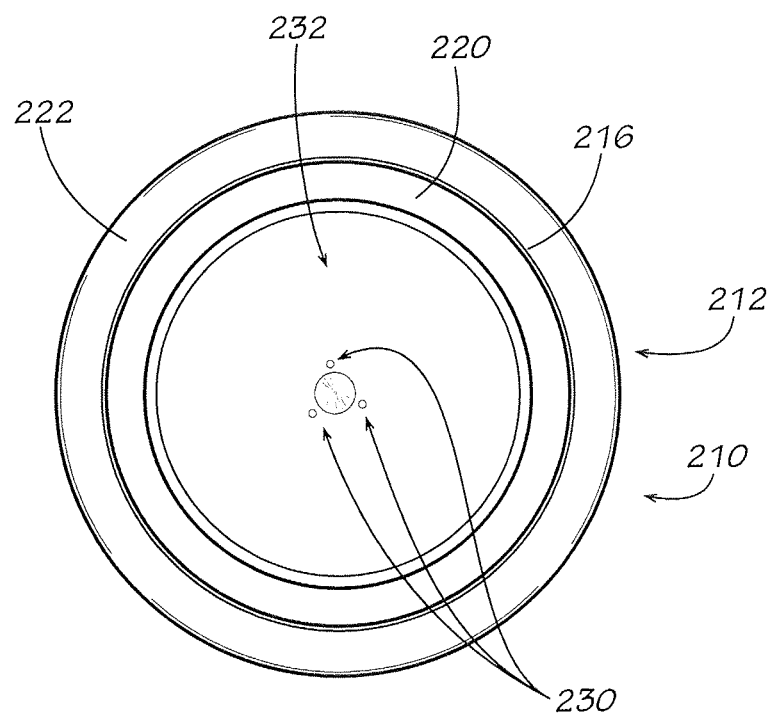
FIG. 5 illustrates a top plan view of the impactor of FIG. 1.

The housing 212 of the impactor 210 contains a plurality of acceleration nozzles 230, as shown in FIGS. 3 and 5. The plurality of acceleration nozzles 230 are found in an impactor nozzle body 232. In one embodiment of the present invention, the impactor nozzle body 232 assists in focusing all air and smaller particles through the acceleration nozzles 230 toward the impaction substrate 240, and more specifically, an impaction plate 242 of the impaction substrate 240, shown in FIGS. 2-3 and 6. The combination of the impactor 210 and the impaction substrate 240 work to remove larger particles from reaching the diffuser stage 300 in order to achieve the dispersion criterion/dispersion curve desired, discussed in more detail below. In an aspect, as illustrated in FIGS. 3 and 5, the acceleration nozzles 230 are found approximate the center of the impactor nozzle body 232, oriented in a position within the impactor 210 above the cyclone 140 and its opening 142 and below and in line with the impaction plate 242 of the impaction substrate 240. The acceleration nozzles 230 can have a desired shape, such as, for example and without limitation, round, circular or slotted. The number of acceleration nozzles 230 can vary in number, as discussed in more detail below.

The plurality of acceleration nozzles 230 can be oriented in a uniform manner within the impact surface 232 below the impaction substrate 240, or can be oriented in a non-uniform manner. Regardless, the acceleration nozzles 230 should be oriented in a manner to ensure that the air in which they direct towards the impaction substrate 240 does not go around the impaction plate 242 but impacts the bottom surface 244 of the impaction plate 242 (see FIG. 6). Likewise, the diameter/width of the impaction plate 242 at the bottom surface 244 can vary, but should be large enough to prevent air directed from the acceleration nozzles 230 from directly going around the bottom surface 244 of the impaction plate 242.

Before being assembled with the impactor 210 and the spacer 280, the bottom surface 244 of the impaction plate 242 of the impaction substrate 240 can be covered with a vacuum grease. In an exemplary aspect, a high vacuum grease from Dow Corning is used. However, other types of vacuum greases may be used in other aspects.

Figure 7:
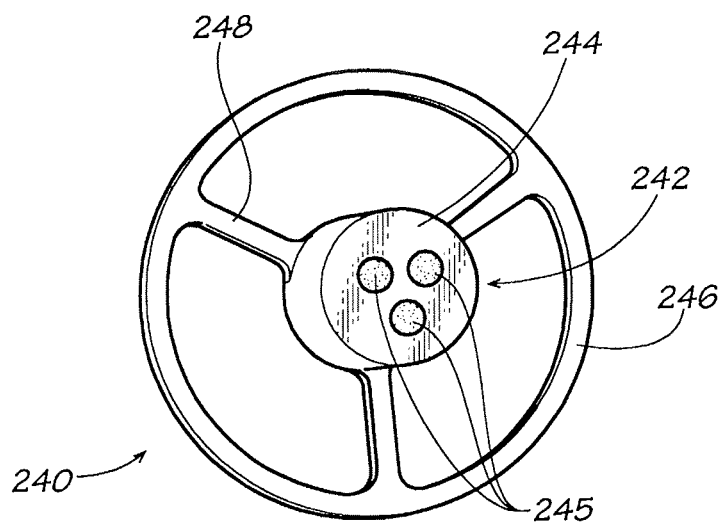

The bottom surface 244 of the impaction plate 242, with the assistance of the vacuum grease, can remove particles from the air as the acceleration nozzles 230 for air into the impactor 210. The vacuum grease collects a portion of the particles that enter into the impactor stage 200, preventing them from bouncing off the bottom surface 244 of the impaction plate 242. As the acceleration nozzles 230 focusing the air towards the bottom surface 244 of the impaction plate 242, the air flow bends at an 90 degree angle to travel past the impaction plate 242, which causes bigger particles to impact the impaction plate 242 and be retained by the vacuum grease (245 as shown in FIG. 7). Smaller particles are carried by the air flow and past the impaction plate 242, traveling on towards the diffuser stage 300.

In another aspect, the acceleration nozzles 230 can comprise a round shape, and are spaced from the impaction plate 242 of the substrate at a distance (S). In addition, the acceleration nozzles 230 can have a width (W) and a throat length ($L_T$). While it is preferable that the width (W) and the throat length ($L_T$) of the plurality of acceleration nozzles 230 are the same, the width and the throat length of each acceleration nozzle may vary in some embodiments of the present invention. In an aspect, the nozzle width (W), the number (n) of acceleration nozzles 230, the nozzle throat length ($L_T$) and the distance (S) between the acceleration nozzles 230 and the impaction plate 242 are configured to remove particles larger than a selected size in order for the diffusion stage 300 to match the selected sampling criterion.

In another aspect, the acceleration nozzles 230 comprise a slotted or rectangular shape, and are spaced from the impaction plate 242 of the substrate at a distance (S). The acceleration nozzles can have a throat length ($L_T$), a width (W), and a slot length ($L_S$), with the smaller value of the two being assigned as the width (W). While it is preferable that the width (W) the throat length ($L_T$), and the slot length ($L_S$) of the plurality of acceleration nozzles 230 are the same, the values of each acceleration nozzle may vary in some embodiments of the present invention. In an aspect, the number (n) of acceleration nozzles 230, the nozzle throat length ($L_T$), the nozzle width (W) and slot length ($L_S$) and the distance (S) between the acceleration nozzles 230 and the impaction plate 242 are configured to remove particles larger than a selected size in order for the diffusion stage 300 to meet the selected sampling criterion.

In an aspect, the configuration of the impactor stage 200, and more specifically the configuration of the components of the impactor 210 and impactor substrate 240 can be based upon determining the 50% cutoff diameter ($d_{50}$) (i.e., where 50% of the particles are collected within the impactor stage 200 and 50% of the particles exit the impactor stage 200) that ensures the diffusion stage 300 operates at the selected sampling criterion. For example, in an exemplary aspect, the impactor stage 200 can be designed to achieve a 50% cutoff diameter ($d_{50}$) of approximately 300 nm at a flow rate Q=2.5 Lpm. In another aspect, the impactor stage 200 can be configured to operate at a given sharpness ($\sigma$) that ensures the diffusion stage 300 operates at the selected sampling criterion. For example, in an exemplary aspect, the impactor stage 200 can be designed to achieve a sharpness of 1.53. In an exemplary aspect, the impactor stage 200 can be designed to achieve a certain 50% cutoff diameter while achieving a desired sharpness ($\sigma$) to ensure that the diffusion stage 300 operates at a collection efficiency that matches the selected sampling criterion.

In another aspect, the design parameters can include the selection of a number (n) of acceleration nozzles with a width (W), operating at a flow rate (Q), to achieve a Reynolds number 500<Re<3000. While the impaction stage 200 can be configured to achieve a Reynolds number outside of the aforesaid range, it is preferable for the impactor stage 200 to be configured to achieve a Reynolds number within the stated range in order for the impactor stage 200 to operate in a more efficient manner. In an exemplary aspect, the number (n) of acceleration nozzles 230 can comprise three round acceleration nozzles 230 with a width (W) of 0.053 cm operating at a flow rate (Q) of 2.5 Lpm. However, in other embodiments of the present invention, the plurality of acceleration nozzles 230 can vary in number dependent on the desired cutoff diameter, as well as the flow rate (Q) and nozzle width (W) (for acceleration nozzles having a slotted design, the smaller of the width and slot length) to achieve a different Reynolds number.

Figure 6:
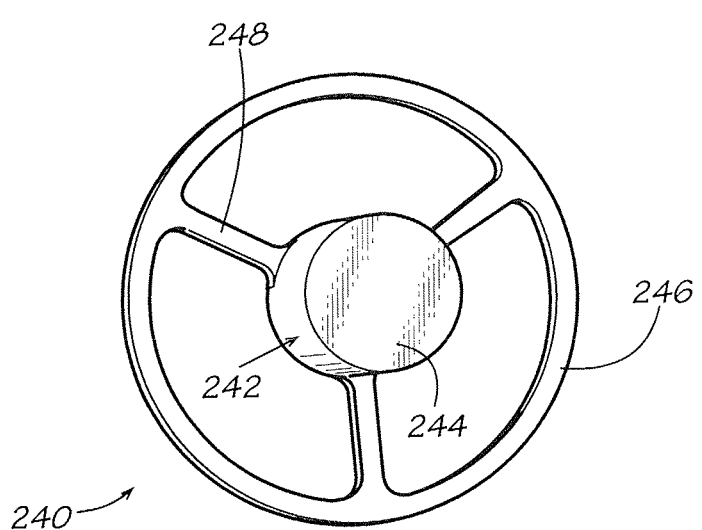
FIGS. 6-7 illustrate a bottom perspective view of the impact substrate of FIG. 1.

As shown in FIGS. 6-7, the impaction substrate 240 includes a support ring 246 that is connected to the impaction plate 242 through connecting supports 248. The support ring 246 is configured to rest on the top end 216 of the housing 212 of the impactor 210, allowing the bottom surface 244 of the impaction plate 242 to rest above the acceleration nozzles 230 when the components of the NRD sampler 10 are assembled. It is preferable that the connecting supports 248 are limited in number to prevent any unnecessary obstructions of the air path through the impact phase 200 to the diffusion stage 300. As shown in FIGS. 6-7, the connecting supports 248 are oriented in a spoke-like fashion, with the connecting supports 248 being of uniform length and width. However, in other embodiments, the connecting supports 248 can make up other orientations.

Figure 1:
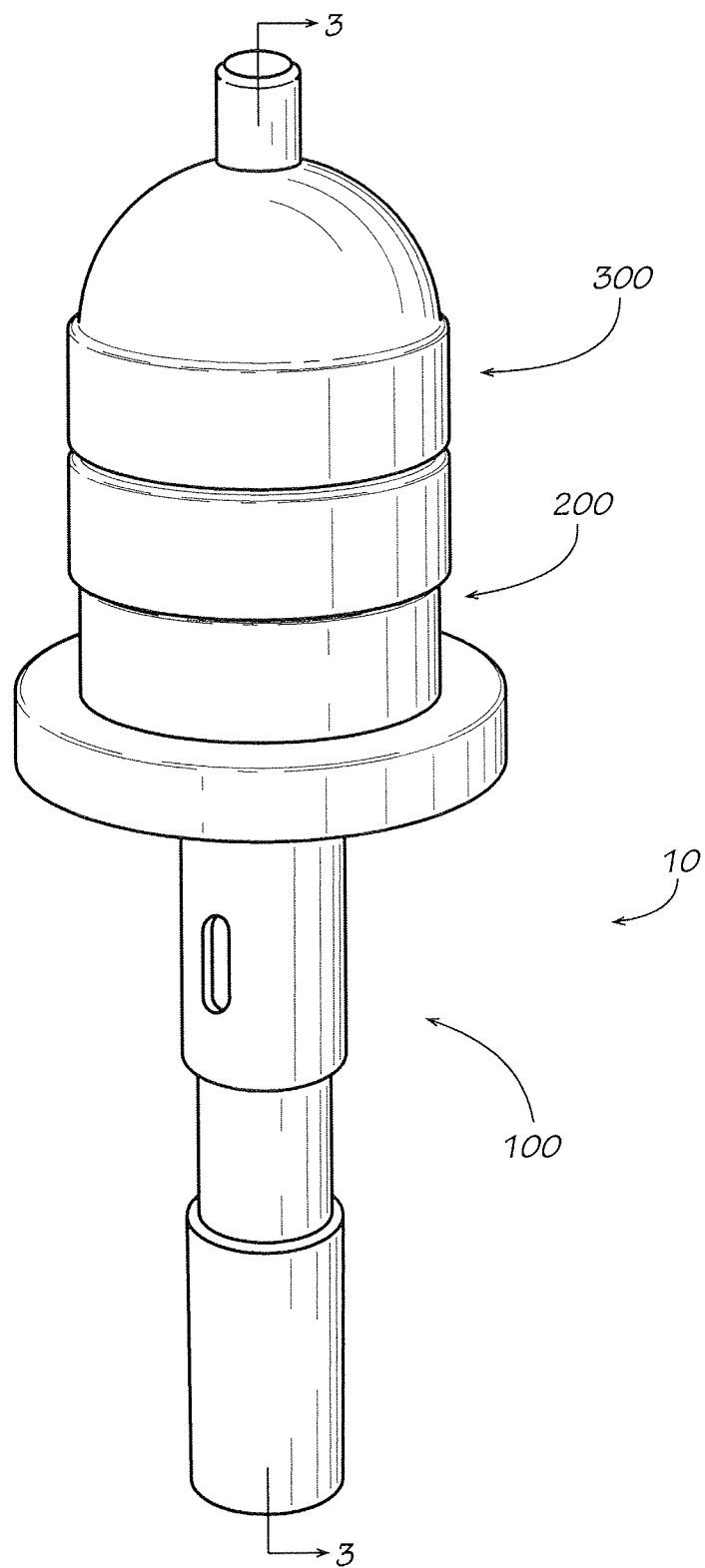
FIG. 1 illustrates a front plan view of a nanoparticle respiratory deposition sampler according to an embodiment of the present invention.
Figure 8:
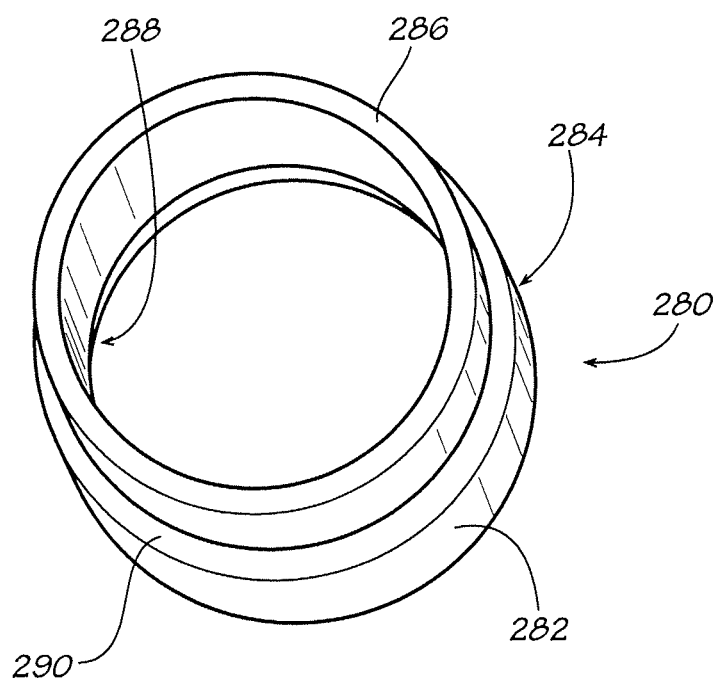
FIG. 8 illustrates a top perspective view of the spacer of FIG. 1.

As shown in FIGS. 1-3 and 8, the spacer 280, in combination with the impactor housing 212, secures the impaction substrate 240 above the acceleration nozzles 230 when assembled. The spacer 280 includes a tubular body 282 with a bottom end 284 and a top end 286. In some embodiments of the present invention, the interior of the tubular body 282 includes an extended ledge 288 that, when combined with the top end 216 of the impactor 210, secures the impaction substrate 240 in place when the spacer 280 and impactor 210 are secured together. The spacer 280 as shown in FIGS. 2-3 and 8 includes an outer ledge 290 that provides a surface for which components of the diffuser stage 300 can rest upon.

Figure 9:
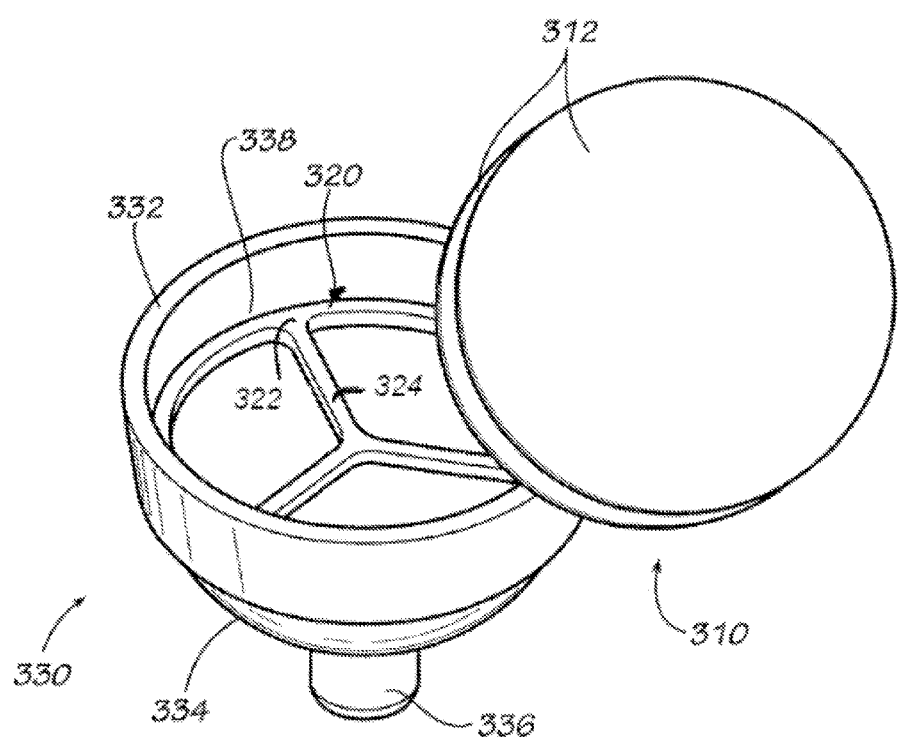
FIG. 9 illustrates a schematic of the assembly of the diffusion stage of FIG. 1.
Figure 10:
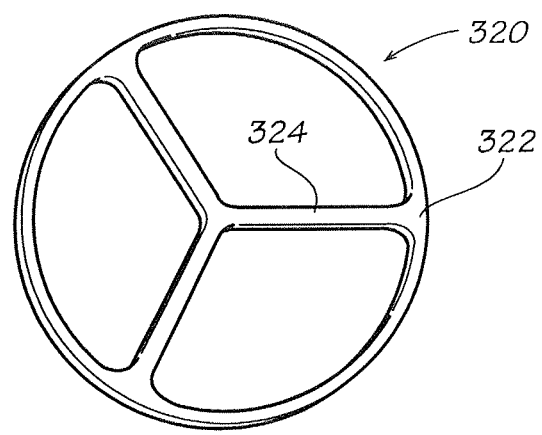
FIG. 10 illustrates a top plan view of the support ring of FIG. 2.
Figure 11:
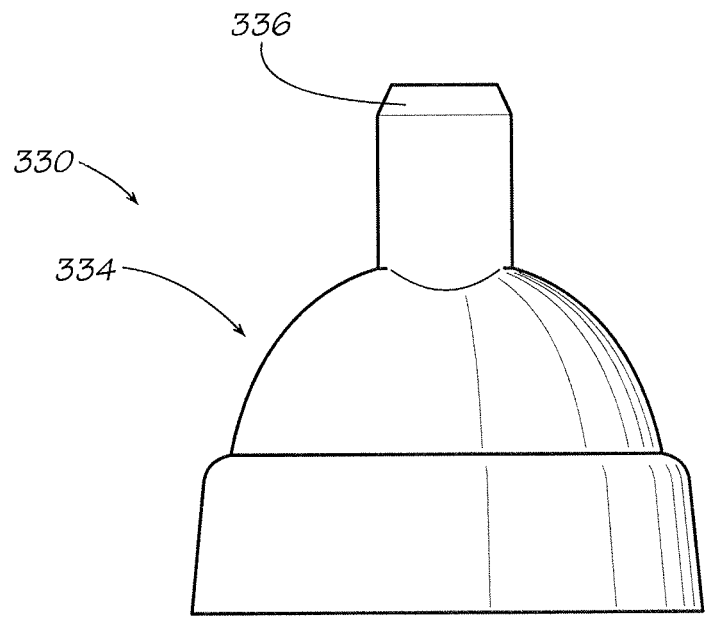
FIG. 11 illustrates a side plan view of the cap of FIG. 1.

As shown in FIGS. 1-3, the diffusion stage 300 is configured such that any remaining airborne particles diffuse into and are collected by the diffusion section 310. The diffusion section 310 collects the particles at a collection efficiency that matches the nanoparticulate collection criteria. The diffusion stage 300 includes a diffusion section 310 engaged by a support ring 320 and contained within a diffuser cap 330. The support ring 320, as shown in FIGS. 9 and 10, includes an outer rim 322 and spokes 324. In other aspects, the support ring 320 can have different components dependent on the composition of the diffusion section 310, discussed in more detail below. The diffusion cap 330, as shown in FIGS. 2, 3, 9, and 11, includes a bottom end 332, a top end 334, an outlet 336 oriented at the top of the top end 334, and an inner ledge 338. In one exemplary aspect, the diffusion section 310 is assembled by placing the support ring 320 on the inner ledge 338 of the cap 330 first, and then placing the diffusion section 310 on the support ring 320, as shown in FIG. 9. The cap 330 is then secured to the spacer 280 of the impactor stage 200. When assembled, the diffusion section 310 is secured between the impaction substrate 230 and the support ring 320, with the bottom end of the cap 332 engaging the top end 216 of the housing 212 of the impactor 210, and the support ring 320 engaging the inner ledge 338 of the diffusion cap 330, preventing the diffusion section 310 from moving within the diffusion cap 330.

Figure 12:
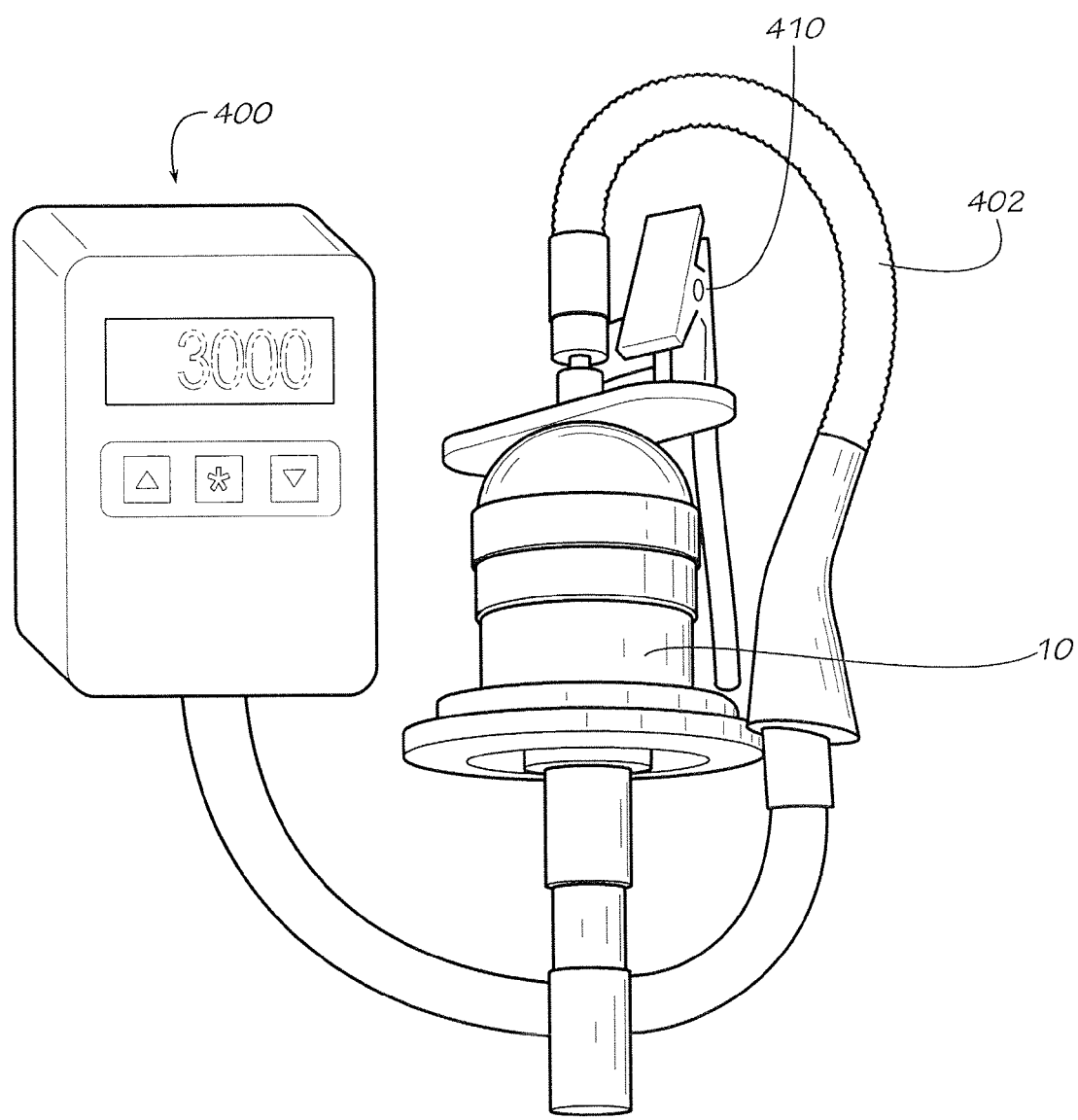
FIG. 12 illustrates a nanoparticle respiratory deposition sampler coupled to a pump according to an embodiment of the present invention.

The outlet 336 is configured to be coupled to an air pump 400. The air pump 400 is connected to the outlet 336 through a tube 402, as shown in FIG. 12. The air pump 400 pulls air through the NRD sampler 10 through the air inlet 120 of the particle size separator 100, through the impactor stage 200, into the diffusion stage 300 and through the diffusion section 310 and out the outlet 336. In a further aspect, the NRD sampler 10, by way of the pump 400, can be configured to operate at a selected airflow rate (Q) and selected pressure drop. For example, and without limitation, the pump 400 can be set to operate at 2.5 Liters per minute ("Lpm"), with a selected pressure drop, such as, for example and without limitation, 3.54 kPa (14.2 in. H$_2$O). For example, when the NRD sampler 10 is employed in human sampling applications, it is contemplated that the selected airflow rate (Q) can be less than about 10 Lpm. However, it is contemplated that the selected airflow rate (Q) can be any airflow rate that cooperates with the impaction stage and the diffusion stage to achieve the desired collection characteristics; it is contemplated that airflow rates above about 10 Lpm, which can be employed with larger pumps and samplers, can provide lower detection limits during chemical analysis.

In other exemplary aspects, it is contemplated that the sampler can be used with a commercially available belt-mounted sampling pump 400 for an extended period of time, such as the duration of a work-shift. An exemplary belt-mounted sampling pump for these purposes is the AirCheck 2000 (SKC Inc., Eighty Four, Pa.). However, the NRD sampler 10 can utilize any known air pumps on the market.

As In the illustrated aspect, the diffusion section 310 of the diffusion stage 300 comprises a plurality of diffusion screens 312. The plurality of diffusion screens 312 can be configured in a stacked position within the diffusion section 310. As illustrated in FIGS. 2-3, the diffusion screens 312 are stacked on one another. However, in other aspects, the diffusion screens 312 can be separated by spacers. In the illustrated aspect, each diffusion screen 312 of the plurality has a uniform filter diameter, pore size and porosity. However, in other aspects, the porosity and pore size of the individual diffusion screens 312 can vary. The material from which the diffusion screens 312 are made can vary among embodiments, including, but not limited to, nylon, PVC thread, carbon fibers, and the like. The material of the diffusion screens 312 is not critical, unless the material is electrostatically charged, which can change the way the diffusion screens 312 collect the particles.

In an exemplary aspect, the diffusion section 310 contains eight diffusion screens 312, each diffusion screen 312 having a filter diameter of 25 mm, pore size of about 11 µm and a porosity of about 6% (e.g., Millipore product Catalogue No. NY1102500). But the number of diffusion screens 312, and the pore size and porosity of the diffusion screens 312, can vary based upon the desired performance of the NRD sampler 10 (e.g., the selected sampling criterion), as well as the other parameters utilized by the NRD sampler 10 (e.g., airflow rate, size and number of nozzles, particle size cutoff values, etc.). It should be appreciated that any changes in the number of screens 312 can correspond to a change in collection characteristics that requires that the collection efficiency curves be determined again experimentally. In use, it is contemplated that characteristics of the particle size separator 100, the impaction stage 200 and the diffusion stage 300, as well as the rate of airflow (Q) (controlled by the pump 400), can be selectively varied and controlled to produce the desired deposition of nanoparticles within the diffusion section 310 of the diffusion stage 300 to match the selected sampling criterion.

In other aspects, the diffusion section 310 can be comprised of diffusion type materials and structures other than diffusion screens 312. In one aspect, the diffusion section 310 can comprise non-metallic components, including, but not limited to, glass beads or microspheres, carbon nanotubes, carbon fibers, threads, and other non-metallic materials having significant surface area, to more readily permit chemical analysis of the nanoparticles. Due to the presence of background metals in some diffusion screens, as the number of screens in the plurality of screens decreases, the ability to conduct chemical analysis of the nanoparticles collected on the screens increases. It is further contemplated that the diffusion stage can comprise any material and have any porosity or pore size that achieves desired nanoparticle collection characteristics. In such embodiments, the support ring 320 can include additional spokes 324 or even a meshed screen itself, or used in conjunction with one or more meshed screens or other similar components in order to retain the material employed by the diffusion section 310.

In exemplary aspects, it is contemplated that the NRD sampler 10 can be lightweight, such as, for example and without limitation, about 60 g. In another aspect, the sampler 10 can be configured for attachment or securement to the clothing of a subject, such as, for example, a conventional lapel mount. In other aspects, the NRD sampler 10 can be configured with a clamp 410 that further secures the components of the NRD sampler 10 together while providing a clip to mount on a subject, as shown in FIG. 12.

Thus, it is contemplated that the NRD sampler 10 combines a particle size separator 100 with an impactor stage 200 and a diffusion stage 300, where nanoparticles deposit for traditional post-sampling analyses. It is further contemplated that the impactor stage 200 can be configured to maintain desirable performance despite worst-case, heavy particle loading by applying the vacuum grease to the bottom surface 244 of the impaction plate 242. In use, it is contemplated that the effective deposition efficiency to the screens of the NRD sampler 10 can be in good agreement with the selected sampling criterion, such as, for example, a NPM sampling criterion. It is still further contemplated that the NRD sampler 10 can be personally portable and compatible with current occupational hygiene sampling techniques. It is still further contemplated that the NRD sampler can easily be deployed in occupational settings as a personal sampler. It is still further contemplated that use of the NRD sampler can be easily integrated into exposure assessment strategies and/or incorporated into epidemiological and toxicological studies where pure nanoparticle or mixed nanoparticle/respirable/inhalable aerosols exist.

In an exemplary application of the disclosed NRD sampler, it is contemplated that, because the NRD sampler is configured to capture only nanoparticles of a sampling medium, cost-efficient bulk analysis techniques can be employed to estimate the concentration of engineered nanoparticles that would deposit in the respiratory tract of a subject.

EXPERIMENTAL EXAMPLES

Nanoparticles can elicit substantially greater toxic effects than larger particles of the same composition. However, the mass of nanoparticles is often obscured by that of larger particles in samples collected with traditional 8-hr, filter-based personal samplers (e.g., respirable samplers).

The experimental example described below relates to an exemplary personal NRD sampler as described herein to selectively collect particles smaller than 300 nm in the manner that they typically deposit in the respiratory system of a subject. A sampling criterion for nanoparticulate matter (NPM) was defined, using the International Commission on Radiological Protection deposition curve, to serve as a target for the development of the sampler. The NPM criterion provided the target collection efficiency, by particle size, for the NRD sampler. The exemplary NRD sampler consisted of a respirable cyclone fitted with an impactor and a diffusion stage that contained eight nylon-mesh screens. The NRD sampler presented here was developed by incorporating a respirable sampler (to eliminate particles larger than 10 μm), an impaction plate (to further remove particles up to 300 nm) and a deposition stage configured such that the remaining nanoparticles deposit onto nylon mesh screens to match this target sampling criterion. The sampler operated at 2.5 Lpm and fit on a worker's lapel. The efficiency of the impactor was tested using sodium chloride aerosol with and without prior loading of the impaction plate to determine its ability to tolerate typical workplace loading without performance disruptions. The cut-point diameter of the impactor was 300 nm with a sharpness σ=1.53. Loading at typical workplace levels was found to have no significant effect on the impactor's performance. The effective deposition of nanoparticles on the mesh screens of the diffusion stage with the respirable cyclone and impactor present was measured by depositing 20, 40, 100, 200 and 500 nm monodisperse ammonium fluorescein particles, which were subsequently recovered and measured with the use of a fluorometer. The effective deposition of the NRD sampler was found to match the NPM sampling criterion, showing that a sample collected with the NRD represented the concentration of nanoparticles deposited in the human respiratory system. The chemical analysis of the nanoparticles deposited on the collection media of the NRD sampler allowed for characterization of the nanoparticles apart from larger background particles.

Development of a Target Size Selection Curve

Particle deposition in all regions of the respiratory tract is shown in FIG. 13. Conventionally, deposition of particles measured experimentally under a wide variety of conditions generally follows the respiratory deposition curve for the average adult under light exercise and nose-breathing conditions presented by the International Commission on Radiological Protection (ICRP). For this reason, the ICRP curve was used in developing the NPM sampling criterion. The region of interest for the NPM curve was all particles smaller than 300 nm, the minimum deposition for submicrometer particles.

The NPM fraction was defined, for a given particle size, as the fraction of those particles that, when inhaled, can deposit in the respiratory system. Therefore, the NPM fraction was a subset of the inhalable particulate matter (IPM) collection efficiency, defined as:

IPM($d$)=0.5[1+exp(−0.06 $d$)] for (0<$d$:≤100 μm), where d is the particle diameter in μm. The collection efficiency for NPM was, therefore, given by:

NPM($d$)=IPM($d$)[1−$F(x)$], where F(x) is the cumulative probability density function of the standardized normal variable x, $$x = \frac{\ln(d/\Gamma)}{\ln(\Sigma)}$$

with Γ=0.04 μm (40 nm), and Σ=3.9. The mathematical form for this criterion was the same as that used for the thoracic and respirable criteria. The value for r represented the particle size associated with 50% deposition, or $d_{so}$ cutoff diameter. This value was selected as the particle size smaller than 300 nm associated with 50% deposition as defined by the ICRP curve. As shown in FIG. 13, in this region $d_{SO}$=40 nm. The value for L was selected by minimizing the sum of squares error between the ICRP total deposition curve and the NPM curve for particles smaller than 300 nm. This minimization was carried out in a MS Excel (Microsoft Corp., Redmond, Wash.) spreadsheet using the solver function.

In The resulting NPM sampling criterion is shown by the solid line in FIG. 13. This criterion provided a rational target for the development of the NRD sampler and ties its performance to the physiologically relevant fractional deposition of nanoparticles in all regions of the respiratory tract. The shallow shape of the collection efficiency curve matched the collection efficiency performance form associated with diffusion techniques (rather than the sharp curve associated with impaction). This allowed the sampler to collect nanoparticles, achieving a sampler pressure drop small enough for use with conventional occupational hygiene belt-mounted sampling pumps.

The final design parameters for the impaction stage are presented in Table 1 and were calculated assuming temperature T=20° C., pressure P=98.6 kPa, aerosol particle density $\rho_p$=1000 kg/m$^3$, air density $\rho_a$=1.2 kg/m$^3$ and air viscosity $\mu$=1.81×10$^{-5}$ Pa-s.

Filtration theory was used to determine the number and mesh size of diffusion screens necessary to match the NPM sampling criterion. The diffusion screens were tightly held in place in the diffusion stage by an aluminum ring with three spokes. Tests of the collection efficiencies of the impactor, both clean and pre-loaded, and the mesh screen diffusion collector were performed in series.

Evaluation of the Impactor Performance

Figure 14:
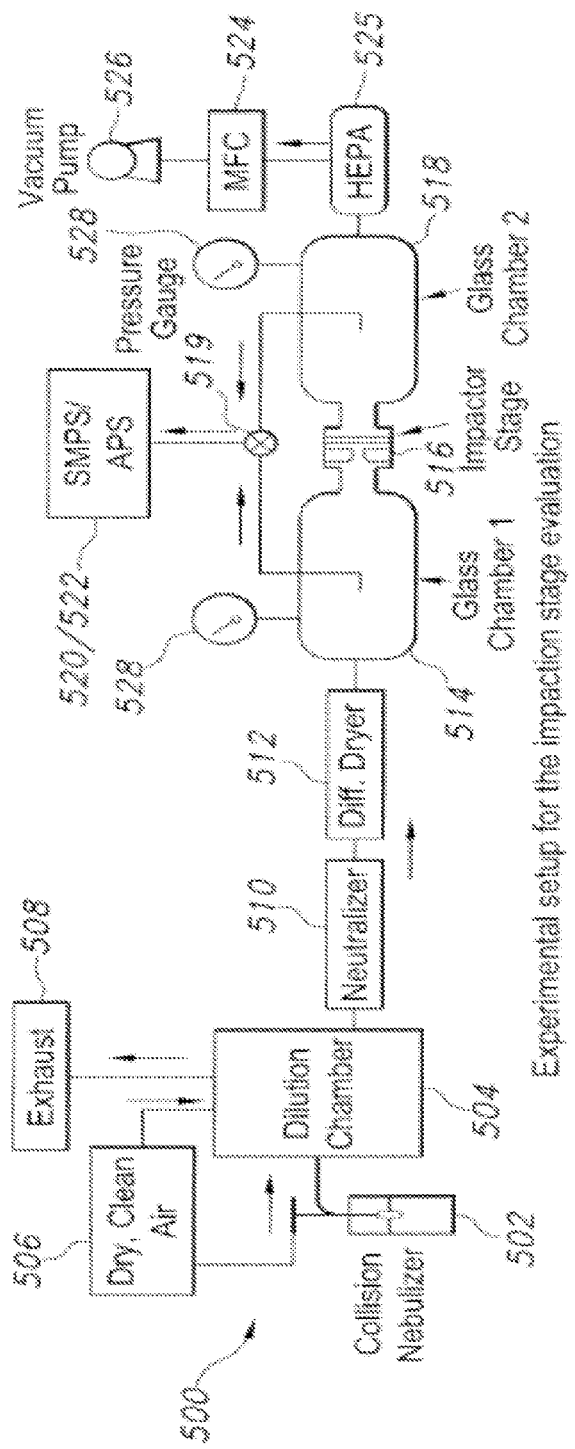
FIG. 14 illustrates a schematic of an evaluation method for the impaction stage of the NRD sampler according to an aspect of the invention.

The experimental setup 500 shown in FIG. 14 was used to evaluate the impaction stage. A three jet Collison nebulizer 502 (BGI, Waltham, Mass.) was used to aerosolize a 16% (by volume) aqueous sodium chloride (Fisher Scientific, Lot No. 028258) solution. The resulting polydisperse aerosol was fed into a dilution chamber 504, mixed with clean, dry air 506 (with exhaust 508 exiting the dilution chamber 504), and passed through a charge neutralizer 510 (Model 3054, TSI Inc., Shoreview, Minn.) and a diffusion dryer 512 (Model 3062, TSI Inc., Shoreview, Minn.). The aerosol was then passed into a 0.002 m$^3$ glass chamber 514, through the impactor stage 516 and into a second identical glass chamber 518.

Using a 3-way switching valve 519, the particle number concentration by size was measured alternately from within the glass chamber 514 upstream ($C_{in}$) and from within the glass chamber 518 downstream ($C_{out}$) of the impactor 516. A scanning mobility particle sizer 520 (SMPS) (Model 3080, TSI Inc., Shoreview, Minn.; airflow=0.3 Lpm) was used to count particles from 15 to 500 nm, and an aerodynamic particle sizer 522 (APS) (Model 3321, TSI Inc. Shoreview, Minn.) was used to count particles from 0.5 to 2 µm. The APS 522 was modified so that the sample entered directly into the aerosol inlet at 1 Lpm. A mass flow controller 524 (MFC) (Model GFC37, Aalborg Instruments & Controls Inc., New York, N.Y.) and a high efficiency particular air filter 525 were used to maintain a constant flow rate of 2.5 Lpm drawn through the impactor 516 with a vacuum pump 526 (Model 4F740A, Gast Manufacturing Inc., Benton Harbor, Mich.). The alternating of measurements upstream and downstream of the impactor 516 was repeated at least three times. A differential pressure gauge 528 (Magnehelic 2020, Dwyer Instruments Inc., Michigan City, Ind.) was connected to each glass chamber 514, 518 to measure the pressure drop across the impactor stage 516.

The collection efficiency (E) of the impactor stage 516 for a given particle size (i) was calculated as: $E_i = 1 - C_{out,i}/C_{in,i}$. The collection efficiency data were fitted with a logistic sigmoidal algorithm (OriginPro v8.5, OriginLab Corporation, Northampton, Mass.) of the form $$E = a_2 + \frac{a_1 - a_2}{1 + \left(\frac{d}{x_0}\right)^p},$$

where a1, a2, xo and p are the coefficients determined by the algorithm. The sigmoidal algorithm allowed accurate estimation of the $d_{50}$, $d_{84}$ and $d_{16}$ of the impactor stage, which correspond respectively with the 50%, 84% and 16% collection efficiencies of the impactor 516. The sharpness (a) of the collection efficiency curve was calculated as:

$$\sigma = \sqrt{\frac{d_{84}}{d_{16}}}$$

Evaluation of Impactor Performance after Loading.

Figure 15:
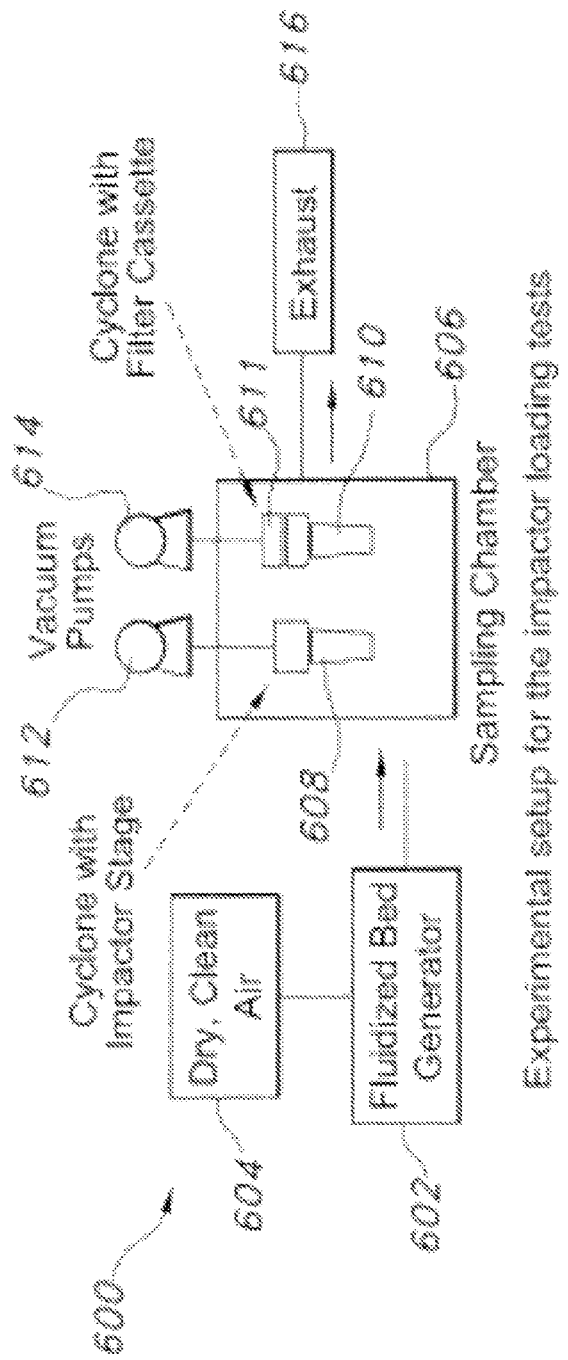
FIG. 15 illustrates a schematic of another evaluation method of the impaction stage of the NRD sampler according to an aspect of the invention.

The performance of the impactor after being loaded with particles was evaluated using the experimental setup 600 shown in FIG. 15. An aerosol composed of fine test dust (Batch #1569, AC Spark Plug Company, Flint, Mich.) with 10-µm volume median diameter was generated using a fluidized bed aerosol generator 602 (Model 3400, TSI Inc., Shoreview, Minn.), mixed with dry, clean air 604, and injected into a 0.02 m$^3$ sampling chamber 606. The aerosol in the chamber 606 was sampled simultaneously with two samplers: 1) the NRD respirable cyclone with the impactor stage downstream 608; and 2) the NRD respirable cyclone 610 with a 37-mm filter cassette containing a Teflo filter 611 (P/N 225-1709, SKC, Inc., Eighty Four, Pa.) with a support pad downstream, pulled through by vacuum pumps 612, 614, before exiting through an exhaust 616. The filter 611 of the NRD respirable cyclone 610 was weighed before and after each test using a microbalance (Model MT5, ISO 9001, Mettler-Toledo Inc., Columbus, Ohio) to determine the mass concentration of dust passing to the impactor.

Two loading levels were targeted to simulate sampling in an environment with 3 mg/m$^3$ passing the cyclone to the impactor for 4 hrs (12 mg/m$^3$×hr) and 8 hrs (24 mg/m$^3$×hr). These values represent worst-case loading of the impactor at the threshold limit value established by the American Conference of Governmental Industrial Hygienists for respirable particles not otherwise specified over times relevant to workplace sampling. Actual loadings measured from the filter sampler for the 4 and 8 hrs loading scenarios were respectively 13.6 mg/m$^3$×hr and 21.5 mg/m$^3$×hr.

After loading, the impaction stage was separated from the cyclone and placed in the previously described impaction stage evaluation setup (FIG. 3). The sampler, now with pre-loaded impaction stages, was again tested with sodium chloride aerosol. The collection efficiency was measured in triplicate following the same procedures outlined above in the impaction stage evaluation. Two replicates of loading followed by collection efficiency measurement were performed for both loading levels. The impaction substrate was cleaned and new grease was applied prior to each loading replicate measure.

Two-way analysis of variance (ANOVA) was performed (Minitab, Minitab Inc., State College, Pa.) on efficiency versus loading and particle size to determine whether the collection efficiency was significantly affected by loading of the impaction substrate ($p \leq 0.05$). The loading levels used in the ANOVA were no previous loading, 13.6 mg/m$^3$×hr, and 21.5 mg/m$^3$×hr.

Effective Deposition to the Screens of the NRD Sampler

Figure 16:
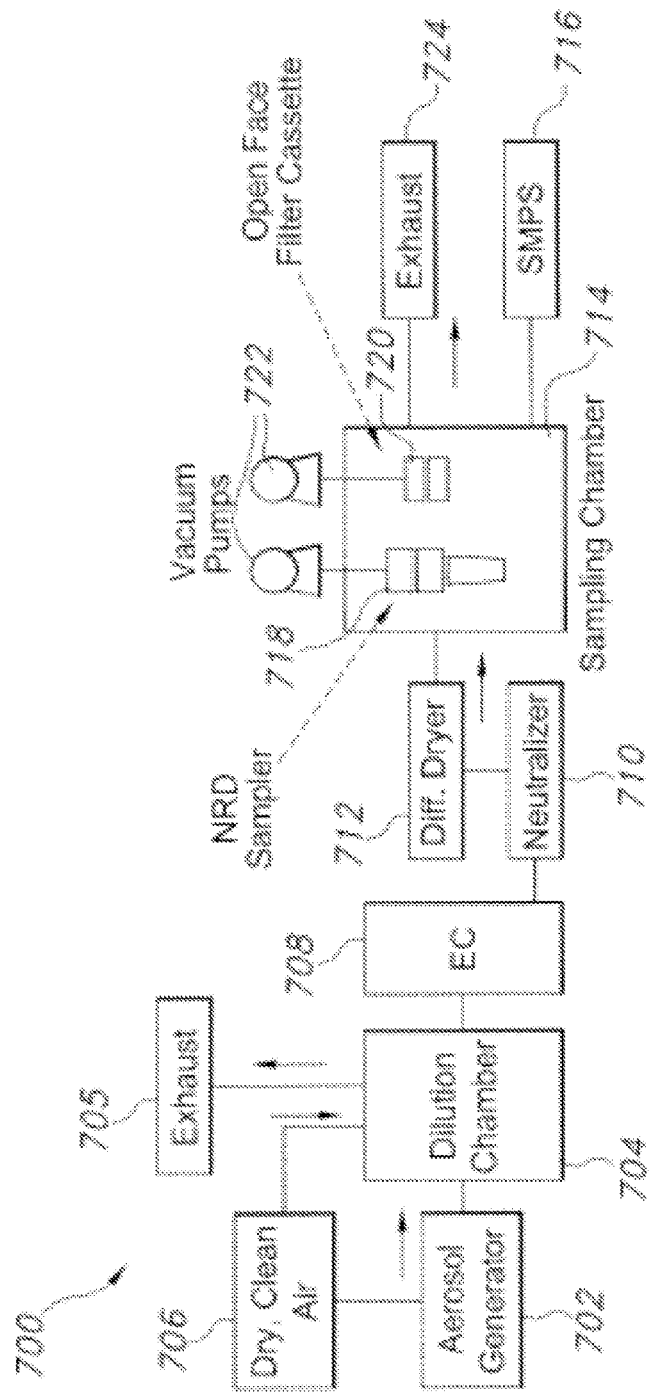
FIG. 16 illustrates a schematic of an evaluation method of the NRD sampler according to an aspect of the invention.

The experimental setup 700 presented in FIG. 16 was used to measure the effective deposition on the diffusion stage of the NRD sampler. Deposition was computed for monodispersed aerosols with mean particle diameters of 20, 40, 100, 200 and 500 nm. To generate seed aerosol for 20-nm tests, an electrospray aerosol generator 702 (Model 3480, TSI Inc, Shoreview, Minn.) was used to aerosolize a 0.01% (by volume) solution of ammonium fluorescein ($C_{20}H_{12}O_5$, Acros Organics, Lot No. A0206621001) in 0.01

N ammonium hydroxide (NH$_4$OH). A three jet Collison-type nebulizer (BGI, Waltham, Mass.) (not shown) was used to nebulize an ammonium fluorescein solution of 0.03% by volume for the 40, 100 and 200-nm tests and 0.15% by volume for the 500-nm tests. The aerosol was fed into a dilution chamber 704 connected to an exhaust 705, mixed with clean dry air 706 and passed through an electrostatic classifier 708 (EC) (Model3071, TSI Inc., Shoreview, Minn.). Because of the difficulty to produce substantial concentrations of small (20 nm) fluorescein particles, the dilution chamber 704 was removed during the generation of the 20-nm aerosol with the electrospray aerosol generator 702. The resulting monodisperse aerosol was neutralized using a neutralizer 710 (Model 3054, TSI Inc., Shoreview, Minn.) and dried using a differential dryer 712 (Model3062, TSI Inc., Shoreview, Minn.) before entering a 0.02 m$^3$ sampling chamber 714. An SMPS 716 (Model5.4 Grimm Technology, Douglasville, Ga.) was used to verify particle size and number concentration in the sampling chamber 712.

The fully assembled NRD sampler 718 (25-mm aluminum cyclone with impaction stage and diffusion stage containing eight nylon mesh screens) and a 37-mm open-face filter cassette containing two Durapore membrane filters with a support pad 720 (P/N DVPPO4700, Millipore, Billerica, Mass.) were placed inside the sampling chamber 714. Two separate vacuum pumps 722 (Omni-5, BGI, Waltham, Mass.) were used to draw an airflow of 2.5 Lpm through each sampler 718, 720 before the remaining mixture exited through the exhaust 724. The vacuum pumps 722 were calibrated with a mass flow meter (Model4146, TSI Inc., Shoreview, Minn.)(not shown) prior to each test. Particles were collected for a period of time ranging between 75 min for the 500 nm particles and 12 hrs for the 20 nm particles to ensure collection of a sufficient quantity of fluorescent material to detect particles on the collection substrate of the diffusion stage.

The amount of fluorescent material deposited on the screens of the diffusion stage and on the filter of the open-face cassette was determined following known analysis protocols. Both substrates were immersed in 4 ml of 0.01 N NH$_4$OH and sonicated (Solid State/Ultrasonic FS-14, Fisher Scientific Inc., Pittsburgh, Pa.) for 10 min. The mass concentration of fluorometric material in the recovered solution was determined using a fluorometer (Modulus 9200, Turner BioSystems, Sunnyvale, Calif.). The deposition efficiency (DD) of particles on the diffusion stage was calculated as $D_D = M_D/M_F$, where $M_D$ is the mass concentration of fluorometric material deposited on the diffusion substrate and $M_F$ is that deposited on the filter of the open-face cassette. These deposition and recovery procedures were repeated three times for each particle size, and new nylon mesh screens and filters were used for each repetition. Mean deposition efficiency of these repetitions was compared to the NPM curve and assessed for fit.

Evaluation of the Impactor Performance.

Figure 17:
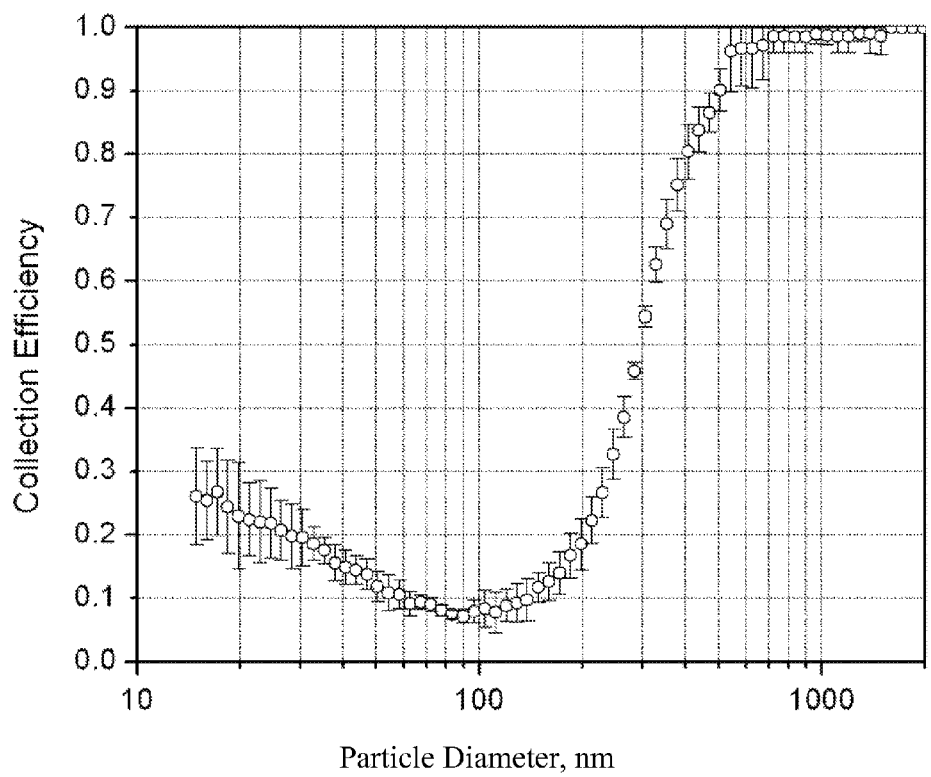
FIG. 17 illustrates a collection efficiency curve of the NRD sampler according to an aspect of the invention.

The collection efficiency curve of the impaction stage is shown in FIG. 17, and the physical characteristics and parameters of the stage are reported in Table 1. The minimum collection efficiency (8%±3%) was observed for particles with a diameter near 100 nm. For particles progressively smaller than this minimum value, collection efficiency gradually increased to 26% (±7%) for 15 nm particles. This increase in efficiency is attributed to diffusion losses that may occur throughout the impactor stage. A similar increase in efficiency due to diffusion was observed in the smallest stages of a recently developed, high flow rate (40 Lpm), portable nanosampler consisting of four impaction stages and an impaction filter. For particles larger that 100 nm, the collection efficiency of the NRD sampler impaction stage rapidly increased to 96% (±6%) for 550 nm particles. Particles in the size range carried sufficient inertia to impact upon the greased impaction plated where they were trapped.

TABLE 1

| Physical Characteristics | | | Flow Parameters | | Experimental Results | | | |
|---|---|---|---|---|---|---|---|---|
| W [cm] | L [cm] | S/W | Re | V [cm/sec] | $d_{50}$ [μm] | $\sqrt{Stk_{50}}$ | Σ | ΔP [kPa] |
| 0.053 | 0.135 | 1.9 | 2212 | 6295 | 0.295 | 0.32 | 1.53 | 2.49 |

Note:
W, nozzle width; L, nozzle lengths; S, impaction plate-to-nozzle distance; Re, Reynolds number; V, nozzle air velocity; $d_{50}$, 50% cutpoint; $\sqrt{Stk_{50}}$, square root of Stokes number at 50% collection efficiency; σ, collection efficiency curve sharpness; ΔP, pressure drop; Stokes number at the 50% cut-off diameter is calculated as:

$$Stk_{50} = \frac{4\rho_p Q d_p^2 Cc}{9\pi n \mu W^3},$$

where $d_p$ is the particle diameter, and Cc is Cunningham slip correction factor.

The characteristic cut-off diameter ($d_{50}$) of the impactor stage was measured to be 295 nm, and the geometric standard deviation (σ) or collection efficiency sharpness was 1.53. This curve was sufficiently sharp to remove particles larger than the cutoff diameter from the airstream. The square root of the Stokes number at the 50% collection efficiency was 0.32 and the pressure drop (ΔP) across the stage was 2.49 kPa. The Reynolds number of the impactor nozzles was 2,212. It is known that the efficiency curve is at its sharpest if the Reynolds number is kept in the 500 to 3,000 range.

Evaluation of Impactor Performance after Loading

The results of the loading tests performed on the impaction stage are summarized in Table 2. When compared to tests with no prior loading, the extent of the effect of particle loading on collection efficiency was negligible as the standard deviations overlapped for all values in Table 2. The results of the two-way ANOVA confirmed that there was not a significant difference in efficiency between loadings (p-value=0.257). The p-value for the interaction term between particle size and loading was close to significant (p-value=0.063) at a 5% alpha level, indicating that with different loadings the efficiency varies at different particle sizes. The greatest reduction of the impactor's collection efficiency was observed at 15 nm, the smallest particle size tested, where efficiency after loading experienced the greatest decrease from E=0.26 without prior loading to E=0.11 after 13.6 mg/m$^3$×hr loading. This reduction was attributed primarily to greater uncertainty in this size channel because of lower particle counts.

TABLE 2

| Particle Diameter [nm] | Prior Impactor Loading [mg/m$^3$ × hr] | | |
|---|---|---|---|
| | 0 | 13.6 | 21.5 |
| | Collection Efficiency (StDev) | | |
| 15 | 0.26 (0.08) | 0.11 (0.08) | 0.15 (0.06) |
| 50 | 0.12 (0.02) | 0.08 (0.04) | 0.07 (0.02) |
| 80 | 0.07 (0.01) | 0.07 (0.04) | 0.04 (0.01) |
| 100 | 0.08 (0.03) | 0.09 (0.02) | 0.06 (0.02) |
| 300 | 0.54 (0.02) | 0.57 (0.01) | 0.57 (0.08) |
| 500 | 0.90 (0.03) | 0.89 (0.01) | 0.86 (0.07) |
| 800 | 0.98 (0.02) | 0.97 (0.01) | 0.92 (0.08) |
| 1000 | 0.99 (0.01) | 0.97 (0.01) | 0.93 (0.07) |

Loading of particles on the impactor plate yielded minimal effects (4% to 6% difference) at the largest particle diameters (>300 nm), where particle bounce had greater potential to affect the performance of the subsequent diffusion stage in the NRD sampler. It is contemplated that bounce of particles larger than 300 nm from the impaction plate could cause particles with substantially greater mass than nanoparticles to pass through the impactor and collect on the diffusion screens. It is further contemplated that this phenomenon could result in a positive sampling bias. The cut-off diameter of the impactor was not substantially shifted after loading ($d_{50}$=265 nm for 13.6 mg/m$^3$×hr loading and 275 nm for 21.5 mg/m$^3$×hr loading). The test dust used in the loading tests contained considerable mass (10 μm volume median diameter) above the $d_{50}$ of the cyclone of 4 μm, which passed through the cyclone and contributed to the loading of the impaction plate. This indicated that the impaction substrate could handle worst-case particle loadings without experiencing substantial shifts in the way that the impactor performed.

The formation of a cone of deposited particles on the impaction surface has been found to shift the efficiency curve to smaller diameter particles. Visual inspection confirmed the absence of these cones after the loading tests performed on the impaction plate of the NRD sampler.

Effective Deposition to the Screens of the NRD Sampler.

Figure 18:
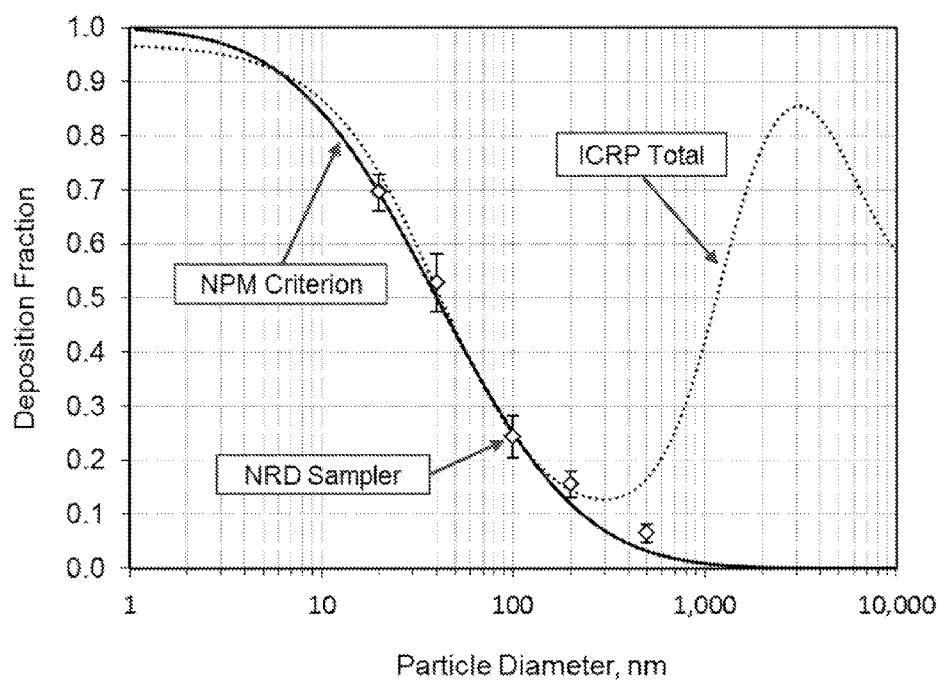
FIG. 18 illustrates the effective deposition of particles to the screens of a NRD sampler according to an aspect of the invention.

The direct measurement of effective deposition of particles to the screens of the NRD sampler is shown in FIG. 18 (open symbols). Deposition was lowest (6%±2%) for 500 nm particles, where the impactor efficiency was at its maximum, and gradually increased with decreasing particle size. FIG. 18 shows that the deposition to the screens was in agreement with the NPM sampling criterion (solid line) within uncertainty for all points with the exception of the 200 and 500 nm particles where it matched within <4%.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention. To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, those skilled in the art will appreciate that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A nanoparticle respiratory deposition sampler, comprising:
   a. an impactor stage comprising:
      i. an impactor comprising a number (n) of acceleration nozzles; and
      ii. an impactor substrate comprising an impact plate, wherein the impaction plate is oriented above the number (n) of acceleration nozzles to remove a portion of nanoparticles from air directed from the number (n) of acceleration nozzles towards the impaction plate;
   b. a diffusion stage configured to be coupled to the impactor stage, wherein the impactor stage and the diffusion stage are further configured to collect nanoparticles based upon a sampling criterion; and
   c. a particle size separator configured to be coupled to the impactor stage opposite the diffusion stage, wherein the nanoparticle respiratory deposition sampler is further configured to be wearable by a subject.

2. The nanoparticle respiratory deposition sampler of claim 1, wherein the sampling criterion comprises a nanoparticulate matter sampling criterion.

3. The nanoparticle respiratory deposition sampler of claim 2, wherein the diffusion stage is configured to operate with a collection efficiency matching the nanoparticulate matter sampling criterion.

4. The nanoparticle respiratory deposition sampler of claim 1, wherein the number (n) of acceleration nozzles and the impaction plate are configured to remove particles larger than a selected size based upon the sampling criterion.

5. The nanoparticle respiratory deposition sampler of claim 4, wherein the diffusion stage is configured to be coupled to a pump configured to pull air through the nanoparticle respiratory deposition sampler at an air flow rate (Q).

6. The nanoparticle respiratory deposition sampler of claim 5, wherein each of the number (n) of acceleration nozzles has a throat length ($L_T$) and a width (W), and wherein the impaction plate is oriented above the number (n) of acceleration nozzles at a distance (S), wherein the number (n) of acceleration nozzles, the throat length ($L_T$) and the width (W) of each acceleration nozzle, the distance (S) between the number (n) of acceleration nozzles and the impaction plate, and the air flow rate (Q) are configured to have the impactor stage remove the particles at a selected 50%-cut-off diameter that is based upon the sampling criterion.

7. The nanoparticle respiratory deposition sampler of claim 5, wherein each of the number (n) of acceleration nozzles has a width (W), wherein the number (n) of acceleration nozzles and the width (W) of each acceleration nozzle are configured to operate at the air flow rate (Q) that produces a Reynolds number between 500<Re<3000.

8. The nanoparticle respiratory deposition sampler of claim 7, wherein the sampling criterion comprises a nanoparticulate matter sampling criterion.

9. The nanoparticle respiratory deposition sampler of claim 8, wherein the nanoparticulate matter sampling criterion matches the deposition of particles in a respiratory tract of a subject.

10. The nanoparticle respiratory deposition sampler of claim 8, wherein the impactor stage is configured to operate at a 50% cutoff diameter of approximately 300 nm.

11. The nanoparticle respiratory deposition sampler of claim 5, wherein the diffusion stage further comprises a diffusion section.

12. The nanoparticle respiratory deposition sampler of claim 11, wherein the diffusion section comprises at least one diffusion screen.

13. The nanoparticle respiratory deposition sampler of claim 1, wherein each acceleration nozzle comprises a circular acceleration nozzle design or a slotted acceleration nozzle design.

14. The nanoparticle respiratory deposition sampler of claim 1, wherein the particle size separator comprises a respirable cyclone.

15. The nanoparticle respiratory deposition sampler of claim 14, wherein the nanoparticle respiratory deposition sampler is further configured to simultaneously operate as a respirable sampler and a nanoparticle deposition sampler.

16. The nanoparticle respiratory deposition sampler of claim 1, wherein the diffusion stage is configured to be coupled to a pump configured to pull air through the nanoparticle respiratory deposition sampler at an air flow rate (Q).

17. The nanoparticle respiratory deposition sampler of claim 1, wherein the nanoparticle respiratory deposition sampler is further configured to be coupled to a pump at the diffusion stage, wherein the nanoparticle respiratory deposition sampler is configured to allow the pump to pull air through the particle size separator into the impactor stage and through the diffusion stage.

18. The nanoparticle respiratory deposition sampler of claim 1, wherein the nanoparticle respiratory deposition sampler is further configured to weigh 60 grams or less.

19. A nanoparticle respiratory deposition sampler comprising:
  a. a particle size separator comprising a respirable cyclone comprising:
    i. an air inlet; and
    ii. a cyclone with a first air tight fastening means;
  b. a impactor stage configured to be coupled to the particle size separator, the impactor stage comprising:
    i. an impactor comprising:
      A. a housing configured to couple to the cyclone through the first air tight fastening means, the housing comprising a second air tight fastening means; and
      B. a number (n) of accelerator nozzles within the housing, wherein each of the number (n) of accelerator nozzles has a throat length ($L_T$) and a nozzle width (W);
    ii. an impactor substrate comprising an impaction plate, wherein the impaction plate is oriented above the number (n) of acceleration nozzles at a distance (S); and
    iii. a spacer configured to couple to the housing of the impactor through the second air tight fastening means to retain the impactor substrate above the impactor and within the spacer; and
  c. a diffusion stage configured to be coupled to the impactor stage opposite the particle size separator, wherein the diffusion stage comprises:
    i. a diffusion section comprising at least one diffusion screen; and
    ii. a cap configured to be coupled to a pump that pulls air through the nanoparticle respiratory deposition sampler by pulling in air through the air inlet of the particle size separator to the cyclone, from the cyclone through the number (n) of acceleration nozzles such that the air bends at 90 degrees and around the impaction plate, and through the at least one diffusion screen, wherein the number (n) of accelerator nozzles, the throat length ($L_T$), the nozzle width (W), and the distance (S) are configured to have the impactor stage and diffuser stage operate at the 50%-cut-off diameter of approximately 300 nm and a sharpness ($\sigma$) of approximately 1.53, wherein the number (n) of acceleration nozzles produce a Reynolds number between $500<Re<3000$, and wherein the diffusion stage is configured to operate at a nanoparticulate matter sampling criterion that matches the deposition of particles in a respiratory tract of a subject; and wherein the nanoparticle respiratory deposition sampler is further configured to be wearable by a subject.

20. The nanoparticle respiratory deposition sampler of claim 19, wherein the nanoparticle respiratory deposition sampler is further configured to weigh 60 grams or less.

\* \* \* \* \*